US010143244B2

(12) United States Patent
Choi (10) Patent No.: US 10,143,244 B2
(45) Date of Patent: Dec. 4, 2018

(54) CLOTHING FOR INFANT HAVING FUNCTIONS OF PREVENTING NECK FROM BENDING BACK AND PROTECTING BACK OF HEAD (71) Applicant: Jung Ho Choi, Bucheon-si (KR)

(72) Inventor: Jung Ho Choi, Bucheon-si (KR)

( * ) Notice: Subject to any disclaimer, the term of this patent is extended or adjusted under 35 U.S.C. 154(b) by 230 days.

(21) Appl. No.: 15/022,542

(22) PCT Filed: Sep. 4, 2014

(86) PCT No.: PCT/KR2014/008349
§ 371 (c)(1),
(2) Date: Mar. 16, 2016

(87) PCT Pub. No.: WO2015/041425
PCT Pub. Date: Mar. 26, 2015

(65) Prior Publication Data
US 2016/0227844 A1  Aug. 11, 2016

(30) Foreign Application Priority Data

Sep. 17, 2013  (KR) .......................... 10-2013-0112181

(51) Int. Cl.
| A41B 13/00 | (2006.01) |
| A61F 5/37 | (2006.01) |
| A41D 13/05 | (2006.01) |
| A47C 7/38 | (2006.01) |

(52) U.S. Cl.
CPC .......... *A41B 13/00* (2013.01); *A41D 13/0512* (2013.01); *A47C 7/383* (2013.01); *A61F 5/3707* (2013.01)

(58) Field of Classification Search
CPC ..... A47C 7/383; A47D 15/005; A61F 5/3707; A41D 13/0512; A41B 13/00
USPC ........................................................ 297/393
See application file for complete search history.

(56) References Cited

U.S. PATENT DOCUMENTS

| 27,058 | A | * | 2/1860 | Lockwood | ............. | A47C 7/383 |
| | | | | | | 297/393 |
| 247,208 | A | * | 9/1881 | Miller | ..................... | A47C 7/383 |
| | | | | | | 128/DIG. 23 |
| 2,973,030 | A | * | 2/1961 | Matthewson | ........... | A61F 5/055 |
| | | | | | | 128/DIG. 23 |
| 3,914,798 | A | | 10/1975 | O'Keefe | | |
| 6,308,345 | B1 | | 10/2001 | Williams, Jr. | | |

(Continued)

FOREIGN PATENT DOCUMENTS

| CN | 1846550 A | 10/2006 |
| CN | 201139300 Y | 10/2008 |

(Continued)

*Primary Examiner* — Milton Nelson, Jr.
(74) *Attorney, Agent, or Firm* — Maschoff Brennan (57) ABSTRACT

Clothing for an infant having functions of preventing the neck from bending back and protecting the back of the head, as suggested in the present invention, has a frame structure body installed within a silicone cover configured in a form of being easily wearable by the infant, and is configured so as to be finished by putting a cushion fabric in the front and the back of the frame structure body and fixing the same with the edge of the silicone cover, thereby being capable of preventing the head of the infant from bending back excessively, and of safely protecting the back of the head of the infant from impact.

11 Claims, 5 Drawing Sheets

(56) References Cited

U.S. PATENT DOCUMENTS

| | | |
|---|---|---|
| 2005/0283884 A1 | 12/2005 | Poole |
| 2011/0197365 A1 | 8/2011 | Wadia |
| 2014/0325741 A1* | 11/2014 | Zaouk .................. B60N 2/4879 |
| | | 2/173 |
| 2016/0183685 A1* | 6/2016 | Kang ..................... A47C 7/383 |
| | | 5/639 |

FOREIGN PATENT DOCUMENTS

| | | |
|---|---|---|
| JP | 2007-284848 A | 11/2007 |
| KR | 20-0124212 Y1 | 10/1998 |
| KR | 20-0333969 Y1 | 11/2003 |
| KR | 20-0335249 Y1 | 12/2003 |
| KR | 20-0362003 Y1 | 9/2004 |
| KR | 10-0558169 | 3/2006 |
| KR | 20-2009-0011833 | 11/2009 |
| KR | 10-2011-0063946 A | 1/2013 |
| KR | 20-2013-0003616 U | 6/2013 |

* cited by examiner

CLOTHING FOR INFANT HAVING FUNCTIONS OF PREVENTING NECK FROM BENDING BACK AND PROTECTING BACK OF HEAD

TECHNICAL FIELD

The present invention relates to clothing for an infant having functions of preventing the neck from bending back and protecting the back of the head, and more particularly, to clothing for an infant having functions of preventing the neck from bending back and protecting the back of the head, which has a frame structure body installed within a silicon cover configured in a form of being easily wearable by the infant, and is configured so as to be finished by putting a cushion fabric in the front and the back of the frame structure body and fixing the same with the edge of the silicon cover, thereby being capable of preventing the head of the infant from bending back excessively and of safely protecting the back of the head of the infant from impact.

BACKGROUND

At the stage of infancy, typical infants are not able to control their heads since their muscle strength is weak, and thus neck or head injury may occur as infant's head bends back. That is, infants' activities increase from 7-8 months of age and infants at this stage have weak leg muscles and their heads are heavier than their bodies. Therefore, when an infant loses balance while playing in a sitting position, the head may bend back excessively, leading to neck injury, and also, when the infant falls backward and hits the head on the floor, brain injury may be caused by the impact to the head and thus fall is very dangerous.

As described above, since the infant's neck bending back excessively or the infant's falling backward may lead to serious accidents, baby product companies have conducted many researches on how to protect infants' heads, and thus a variety of baby products have been developed and are being sold.

That is, as related-art baby products which are being sold in the markets to protect infants' heads or necks, a band type product which can be strapped around infant's head, a head protection air mat into which air is injected, a cushion type product which is provided with a seating portion seated around infant's neck and a pair of cushion portions formed at both sides of the seating portion, etc., are normally used. Korean Patent Publication No. 10-2011-0063946 discloses a neck protection pad which can be installed and used in daily life and in a vehicle seat, and Korean Utility Model Publication No. 20-2013-0003616 discloses a neck/waist protection pad for an infant.

As described above, the baby products which are normally being sold in the markets or the related-art baby products disclosed in the prior art documents only function as cushioning members to protect infant's neck or head from impact which may be caused when the infant falls or hits the floor, and thus have limitation.

SUMMARY

One or more exemplary embodiments provide clothing for an infant having functions of preventing the neck from bending back and protecting the back of the head, which has a frame structure body installed within a silicon cover configured in a form of being easily wearable by the infant, and is configured so as to be finished by putting a cushion fabric in the front and the back of the frame structure body and fixing the same with the edge of the silicon cover, thereby being capable of preventing the head of the infant from bending back excessively and of safely protecting the back of the head of the infant from impact.

One or more exemplary embodiments also provide clothing for an infant having functions of preventing the neck from bending back and protecting the back of the head, which has a head base plate of a frame structure body configured to be tilted backward within a range of 5-60 degrees according to whether the infant is setting or crawling, and thus does not limit infant' motions without causing a sense of irritation since the head base plate is not normally in contact with the infant's head, and is configured to support and protect the infant's head only when the infant loses balance and thus the infant's head bends back excessively, or when the infant falls backward, thereby improving convenience of use.

One or more exemplary embodiments also provide clothing for an infant having functions of preventing the neck from bending back and protecting the back of the head, which has a horizontal core base plate integrally formed with a lower portion of a vertical core base plate in a frame structure body, thereby preventing the lower portion of the vertical core base plate from hitting the infant's back and thus hurting the back when the infant's neck bends back, and is configured to include the frame structure body, and thus can perform a function of stably maintaining an infant's moving position by an infant's motion, in addition to the function of a cushioning member.

Technical Solution

According to an aspect of an exemplary embodiment, there is provided clothing for an infant having functions of preventing the neck from bending back and protecting the back of the head, the clothing including: a frame structure body configured to include: a head base plate for supporting the head of the infant in response to the head of the infant bending back excessively; a vertical core base plate hinged to the head base plate by means of a bar-shaped hinge member; and a horizontal core base plate integrally formed with a lower end of the horizontal core base plate in a perpendicular direction; a silicon cover configured to have the frame structure body accommodated therein, and form an entire exterior of the clothing for the infant; and a cushion fabric installed in a front and a back of the frame structure body installed within the silicon cover to form a cushion layer so as not to prevent the frame structure body from being in contact with the infant.

The silicon cover may be finished by fixing the cushion fabric which is installed in the front and the back of the frame structure body to form the cushion layer with an edge of the silicon cover.

The silicon cover may further include harness rings formed at both shoulder portions and at both side surfaces of left and right wings of the silicon cover forming the entire exterior of the clothing for the infant, and wearing members configured by strap members may be connected with the harness rings to be wearable by the infant.

The frame structure body may further include a stopper member which is installed on the vertical core base plate hinged to the head base plate to be inclined backward by 60 degrees.

The frame structure body may further include a spring hinge member which is installed between the head base plate and the stopper member to adjust an inclination angle of the head base plate.

The vertical core base plate may further include a shoulder fixing base which extends from a lower end of a part to which the bar-shaped hinge member is secured toward both sides.

The head base plate may be configured to be tilted backward within a range of 5-60 degrees with reference to the vertical core base plate to be suitable for an infant who is able to sit or an infant who is able to crawl.

The head base plate may be configured in a U-shape so as to support and protect the neck and the back of the head of the infant.

The horizontal core base plate may function as a support so as to prevent a lower portion of the vertical core base plate from hitting the back of the infant and thus hurting the back when the neck of the infant bends back.

Favorable Effects

According to exemplary embodiments of the present disclosure, the clothing for the infant having the functions of preventing the neck from bending back and protecting the back of the head has the frame structure body installed within the silicon cover configured in the form of being easily wearable by the infant, and is configured so as to be finished by putting the cushion fabric in the front and the back of the frame structure body and fixing the same with the edge of the silicon cover, thereby being capable of preventing the head of the infant from bending back excessively and of safely protecting the back of the head of the infant from impact.

In addition, according to exemplary embodiments of the present disclosure, the clothing for the infant having the functions of preventing the neck from bending back and protecting the back of the head has the head base plate of the frame structure body configured to be tilted backward within a range of 5-60 degrees according to whether the infant is setting or crawling, and thus does not limit infant' motions without causing a sense of irritation since the head base plate is not normally in contact with the infant's head, and is configured to support and protect the infant's head only when the infant loses balance and thus the infant's head bends back excessively, or when the infant falls backward, thereby improving convenience of use.

In addition, according to exemplary embodiments of the present disclosure, the clothing for the infant having the functions of preventing the neck from bending back and protecting the back of the head has the horizontal core base plate integrally formed with the lower portion of the vertical core base plate in the frame structure body, thereby preventing the lower portion of the vertical core base plate from hitting the infant's back and thus hurting the back when the infant's neck bends back, and is configured to include the frame structure body, and thus can perform a function of stably maintaining an infant's moving position by an infant's motion, in addition to the function of a cushioning member.

EXPLANATION OF SIGNS

100: Clothing for infant
110: Frame structure body
111: Head base plate
112: Bar-shaped hinge member
113: Vertical core base plate
114: Horizontal core base plate
115: Stopper member
116: Spring hinge member
117: Shoulder fixing base
120: Silicon cover
121: Harness ring
122: Wearing member
130: Cushion fabric

DETAILED DESCRIPTION OF EXEMPLARY EMBODIMENTS OF THE INVENTION

Hereinafter, exemplary embodiments will be explained in detail with reference to the accompanying drawings so that a person skilled in the art could easily embody the present invention. However, in explaining exemplary embodiments of the present invention in detail, well-known functions or constructions are not described in detail since they would obscure the invention in unnecessary detail. In addition, the same reference numerals are used for parts having similar functions and operations throughout the drawings.

In addition, throughout the specification, when an element is "connected with" another element, the element may be "directly connected with" another element, and also the element may be "indirectly connected with" another element" via an intervening element between the element and another element. In addition, the term "including an element" do not preclude the presence or addition of other elements and further include other elements unless the context clearly indicates otherwise.

Figure 1:
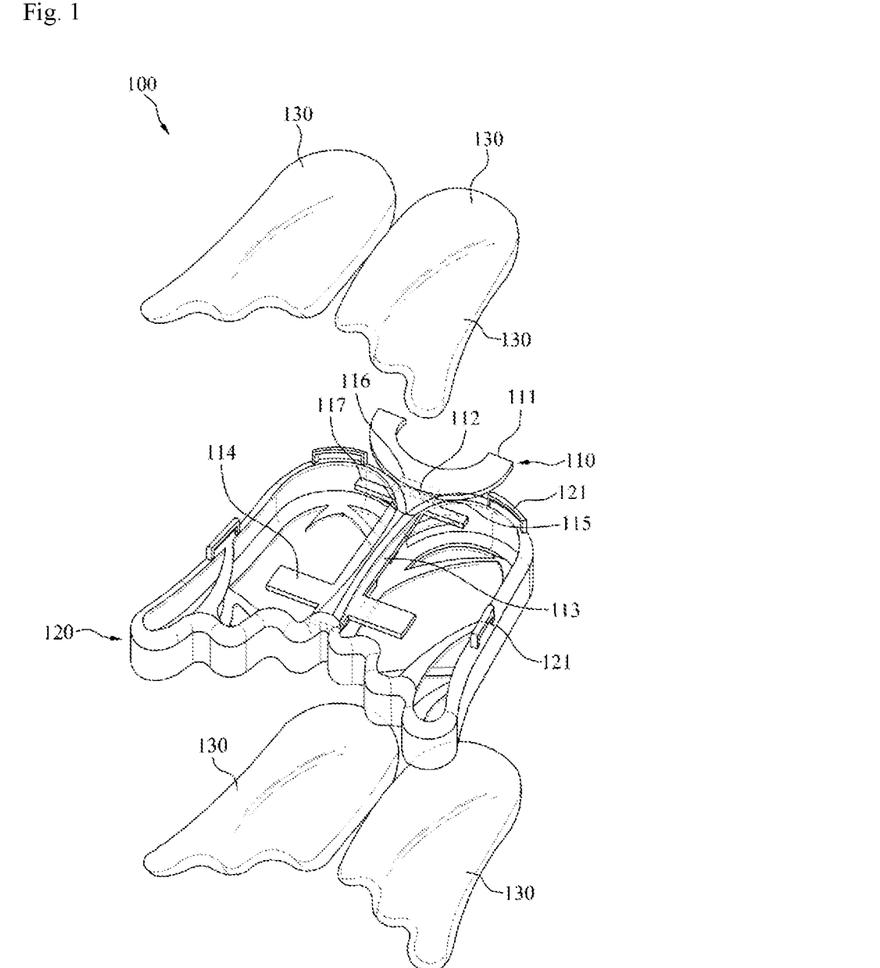
FIG. 1 is an exploded perspective view showing a configuration of clothing for an infant having functions of preventing the neck from bending back and protecting the back of the head according to an exemplary embodiment of the present invention.
Figure 2:
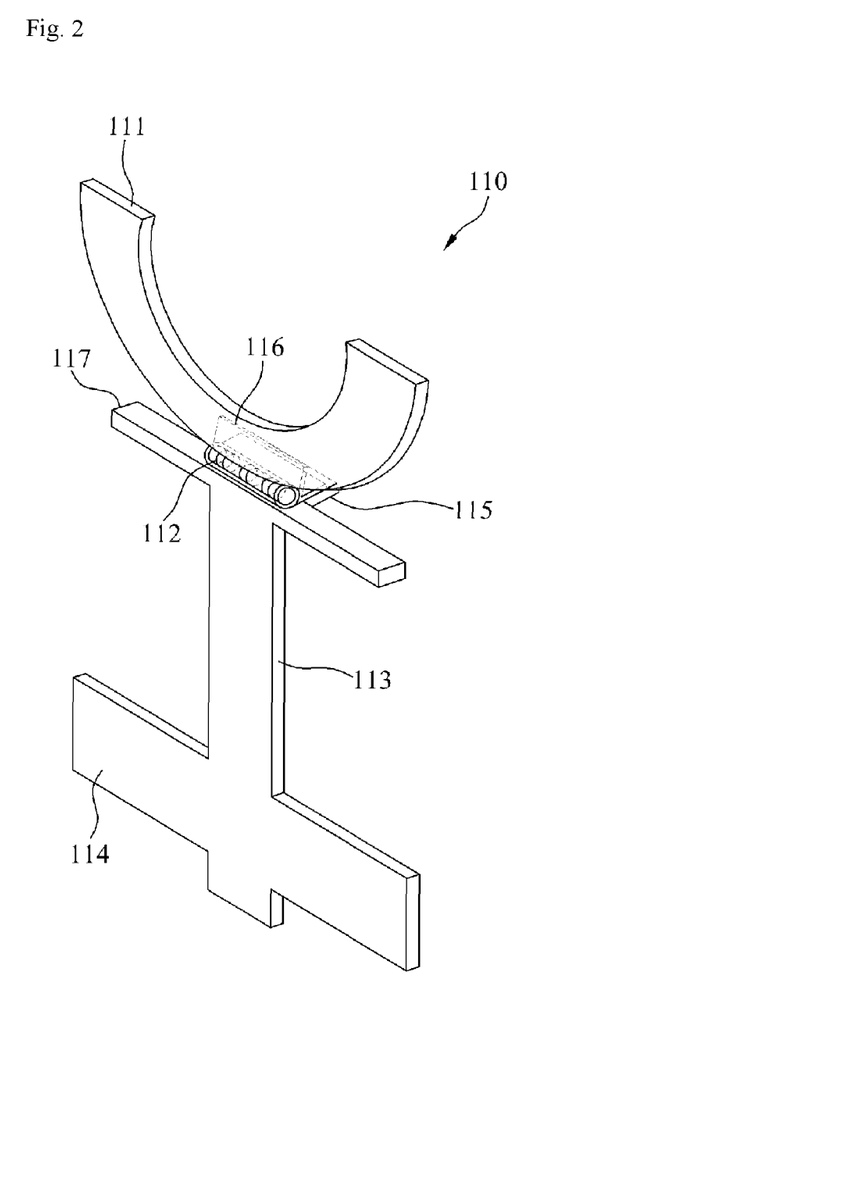
FIG. 2 is a perspective view showing a configuration of a frame structure body which is applied to the clothing for the infant having the functions of preventing the neck from bending back and protecting the back of the head according to an exemplary embodiment of the present invention.

FIG. 1 is an exploded perspective view showing a configuration of clothing for an infant having functions of preventing the neck from bending back and protecting the back of the head according to an exemplary embodiment of the present invention, and FIG. 2 is a perspective view showing a configuration of a frame structure body which is applied to the clothing for the infant having the functions of preventing the neck from bending back and protecting the back of the head according to an exemplary embodiment of the present invention. As shown in FIG. 1 or 2, the clothing 100 for the infant having the functions of preventing the neck from bending back and the protecting the back of the head according to an exemplary embodiment of the present invention may include a frame structure body 110, a silicon cover 120, and a cushion fabric 130.

Figure 4:
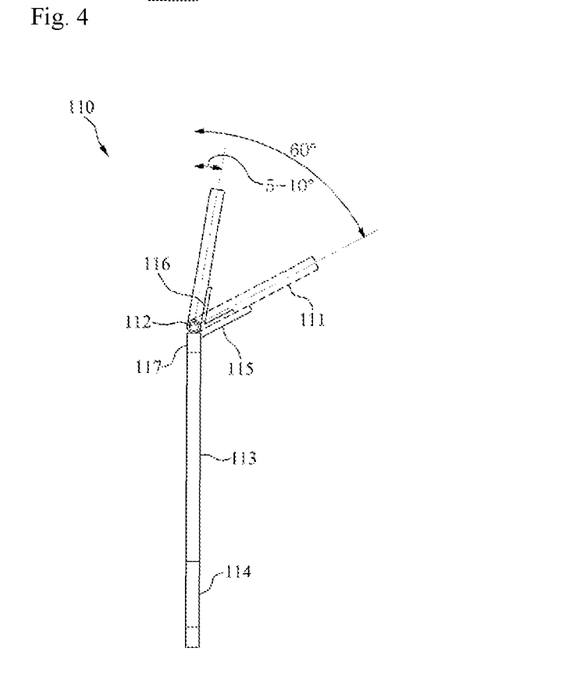
FIG. 4 is a view showing a lateral configuration of the frame structure body which is applied to the clothing for the infant having the functions of preventing the neck from bending back and protecting the back of the head according to an exemplary embodiment of the present invention.

The frame structure body 110 may include a head base plate 111 which is able to support infant's head in response to the infant's head bending back excessively, a vertical core base plate 113 which is hinged to the head base plate 111 by means of a bar-shaped hinge member 112, and a horizontal core base plate 114 which is integrally formed with the lower end of the vertical core base plate 113 in a perpendicular direction. Herein, as shown in FIG. 2, the head base plate 111 of the frame structure body 110 may be formed in a U-shape so as to support and protect the infant's neck and back of the head, but is not limited to this. The head base plate 111 may be formed in various shapes such as a semicircular shape, an oval shape, a circular shape, etc. In addition, as shown in FIG. 4, the head base plate 111 may be configured to be tilted backward within a range from 5 to 60 degrees with reference to the vertical core base plate 113 to be suitable for an infant who is able to sit or an infant who is able to crawl. In particular, the head base plate 111 may be configured to be tilted within a range of 5-10 degrees in the case of an infant who is able to sit.

In addition, the frame structure body 110 may further include a stopper member 115 which is installed on the vertical core base plate 113 hinged to the head base plate 111 to be inclined backward by 60 degrees. Herein, the stopper member 115 may be implemented in one of a configuration in which the stopper member 115 is integrally formed with the vertical core base plate 113 by extending therefrom, or a configuration in which the stopper member 115 is installed on the vertical core base plate 113 to be inclined by 60 degrees. The stopper member 115 fixes the head base plate 111 so as not to be tilted by more than 60 degrees with reference to the vertical core base plate 113, thereby being capable of preventing brain injury from occurring when the infant falls backward. In addition, the horizontal core base plate 114 may function as a support so as to prevent the lower portion of the vertical core base plate 113 from hitting the infant's back and thus hurting the back when the infant's neck bends back.

In addition, the frame structure body 110 may further include a spring hinge member 116 which is installed between the head base plate 111 and the stopper member 115 to adjust an inclination angle of the head base plate 111. The spring hinge member 116 is securely installed between the head base plate 111 and the stopper member 115, and can be elastically maintained when the infant's head bends back and is brought into contact with the head base plate 111. Herein, the spring hinge member 116 may be securely attached by using a screwing method or a 3M double-sided tape.

In addition, the vertical core base plate 113 of the frame structure body 110 may further include a shoulder fixing base 117 which extends from a lower end of a part to which the bar-shaped hinge member 112 is secured toward both sides.

The silicon cover 120 is installed in a form of accommodating therein the frame structure body 110, which includes the head base plate 111, the bar-shaped hinge member 112, the vertical core base plate 113, the horizontal core base plate 114, the stopper member 115, the sprinting hinge member 116, and the shoulder fixing base 117, and is configured to form the entire exterior of the clothing 100 for the infant. As shown in FIG. 1, the silicon cover 120 may be finished by fixing the cushion fabric 130 installed to form a cushion layer on the front and the back of the frame structure body 110 with the edge of the silicon cover 120. That is, the silicon cover 120 may be configured by putting one layer of the cushion fabric 130, which serves as a cushion, in each of the front and the back of the frame structure body 110 installed within the silicon cover 120, and by fixing the frame structure body 110 and the cushion fabric 130 using the edge of the silicon cover 120. In addition, the silicon cover 120 may further include harness rings 121 formed at both shoulder portions and at both side surfaces of left and right wings of the silicon cover 120 forming the entire exterior of the clothing 100 for the infant, and wearing members 122 which are configured by strap members are connected with the harness rings 121, so that the wearing members 122 can be worn by the infant.

The cushion fabric 130 is installed in the front and the back of the frame structure body 110 installed within the silicon cover 120, and is configured to form a cushion layer to prevent the frame structure body 110 from being in contact with the infant. As described above, the cushion fabric 130 may be finished by being installed in the front and the back of the frame structure body 110 in the state in which the frame structure body 110 is installed within the silicon cover 120, and by being fixed through the edge of the silicon cover 120.

Figure 3:
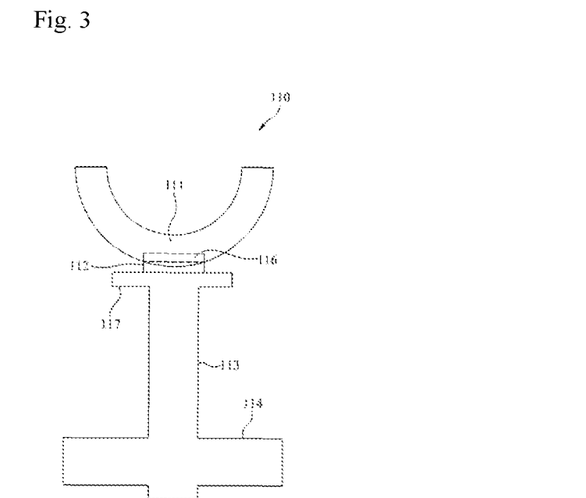
FIG. 3 is a view showing a front configuration of the frame structure body which is applied to the clothing for the infant having the functions of preventing the neck from bending back and protecting the back of the head according to an exemplary embodiment of the present invention.

FIG. 3 is a view showing a front configuration of the frame structure body which is applied to the clothing for the infant having the functions of preventing the neck from bending back and protecting the back of the head according to an exemplary embodiment of the present invention, and FIG. 4 is a view showing a lateral configuration of the frame structure body which is applied to the clothing for the infant having the functions of preventing the neck from bending back and protecting the back of the head according to an exemplary embodiment of the present invention. As shown in FIGS. 3 and 4, the frame structure body 110 has the head base plate 111 and the vertical core base plate 113 hinged to each other by means of the bar-shaped hinge member 112, and has the horizontal core base plate 114 integrally formed with the lower portion of the vertical core base plate 113. Herein, the bar-shaped hinge member 112 has a hinge configuration having a stopper embedded therein, and serves to allow the head base plate 111 to be easily tilted, and the angle of the head base plate 111 may be adjusted within a range of 5-60 degrees as shown in FIG. 4. In this case, the reason why the angle of the head base plate 111 is adjusted within the range of 5-60 degrees is that an sitting infant is not in contact with the head base plate 111 at 5-10 degrees, and a crawling infant is not in contact with the head base plate 111 at 60 degrees when the infant raises the head. That is, the head base plate 111 can prevent the infant from being in contact with the head base plate 111 at the angle of 5-10 degrees, and can prevent brain injury of the infant by fixing the infant's head so as not to bend by more than 60 degrees.

The present invention is configured by a design which allows the head base plate 111 to be moved within 5-60 degrees.

Figure 5:
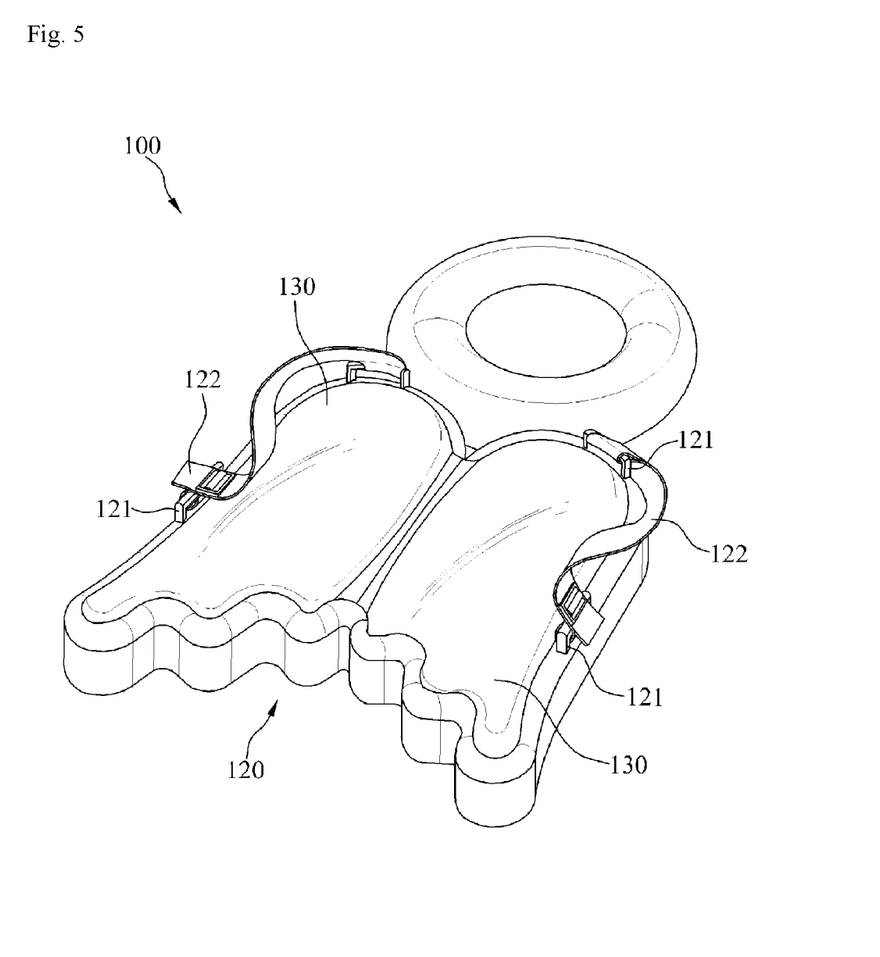
FIG. 5 is a perspective view showing the configuration of the clothing for the infant having the functions of preventing the neck from bending back and protecting the back of the head according to an exemplary embodiment of the present invention.

FIG. 5 is a perspective view showing the configuration of the clothing for the infant having the functions of preventing the neck from bending back and protecting the back of the head according to an exemplary embodiment of the present invention. As shown in FIG. 5, the clothing 100 for the infant has the frame structure body 110 installed within the silicon cover 120 configured in a form of being easily wearable by the infant, and is finished by putting the cushion fabric 130 in the front and the back of the frame structure body 110 and fixing the same with the edge of the silicon cover 120. As described above, since the clothing 100 for the infant has the frame structure body 110 installed within the silicon cover 120, and is configured so as to be finished by putting the cushion fabric 130 having a cushion layer function in the front and the back of the frame structure body 110 and fixing the same through the edge of the silicon cover 120 without a normal sewing process, a manufacturing process such as sewing can be omitted, and also, the finishing process can be securely and simply implemented with a simple design. The silicon cover 120 which forms the entire exterior of the clothing 100 for the infant according to the present invention is configured in the form of angel's wings as shown in FIG. 1 or 5, but is not limited to this and it will be understood that the silicon cover 120 may be configured in various shapes.

Figure 6:
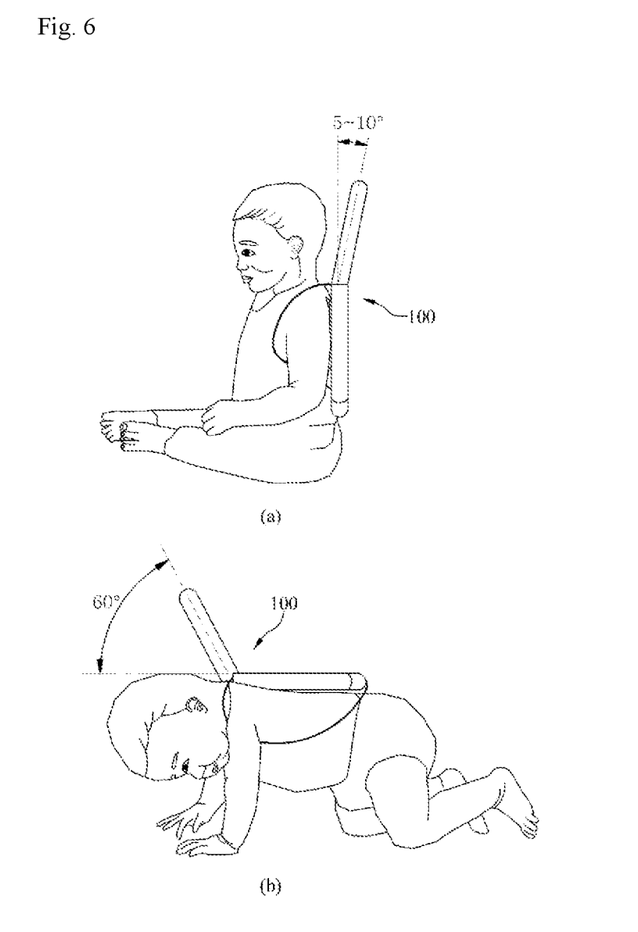
FIG. 6 is a view showing an infant wearing the clothing for the infant having the functions of preventing the neck from bending back and protecting the back of the head according to an exemplary embodiment of the present invention.

FIG. 6 is a view showing an infant wearing the clothing for the infant having the functions of preventing the neck from bending back and protecting the back of the head according to an exemplary embodiment of the present invention. View (a) of FIG. 6 illustrates an infant which is sitting and playing while wearing the clothing for the infant according to the present invention, and view (b) of FIG. 6 illustrates an infant which is crawling on a floor while wearing the clothing for the infant according to the present invention.

As described above, the clothing for the infant having the functions of preventing the neck from bending back and protecting the back of the head according to an exemplary embodiment of the present invention is a safety product for an infant to support and protect the infant's neck and head, and does not limit infant' motions without causing a sense of irritation since the head base plate is not normally in contact with the infant's head, and is configured to support and protect the infant's head only when the infant loses balance and thus the infant's head bends back excessively, or when the infant falls backward. That is, the clothing for the infant of the present invention is configured to include the frame structure body, and thus can perform a function of stably maintaining an infant's moving position by an infant's motion, in addition to the function of a cushioning member.

While exemplary embodiments have been particularly shown and described above, it will be understood by those of ordinary skill in the art that various changes in form and details may be made therein without departing from the spirit and scope of the present invention as defined by the following claims.

The invention claimed is:

1. Clothing for an infant having functions of preventing the neck from bending back and protecting the back of the head, the clothing comprising:

a frame structure body configured to comprise: a head base plate for supporting the head of the infant in response to the head of the infant bending back excessively; a vertical core base plate hinged to the head base plate by means of a bar-shaped hinge member; and a horizontal core base plate integrally formed with a lower end of the vertical core base plate in a perpendicular direction with respect to the vertical core base plate;

a silicon cover configured to have the frame structure body accommodated therein, and form an entire exterior of clothing for the infant; and a cushion fabric installed in a front and a back of the frame structure body installed within the silicon cover to form a cushion layer so as to prevent the frame structure body from being in contact with the infant.

2. The clothing of claim 1, wherein the silicon cover is finished by fixing the cushion fabric which is installed in the front and the back of the frame structure body to form the cushion layer with an edge of the silicon cover.

3. The clothing of claim 2, wherein the frame structure body further comprises a stopper member which is installed on the vertical core base plate hinged to the head base plate to be inclined backward by 60 degrees.

4. The clothing of claim 2, wherein the silicon cover further comprises harness rings formed at shoulder portions of the silicon cover and at side surfaces of left and right wings of the silicon cover forming the entire exterior of the clothing for the infant, and wherein wearing members configured by strap members are connected with the harness rings to be wearable by the infant.

5. The clothing of claim 4, wherein the frame structure body further comprises a stopper member which is installed on the vertical core base plate hinged to the head base plate to be inclined backward by 60 degrees.

6. The clothing of claim 1, wherein the frame structure body further comprises a stopper member which is installed on the vertical core base plate hinged to the head base plate to be inclined backward by 60 degrees.

7. The clothing of claim 6, wherein the head base plate is configured to be tilted backward within a range of 5-60 degrees with reference to the vertical core base plate to be suitable for an infant who is able to sit or an infant who is able to crawl.

8. The clothing of claim 7, wherein the head base plate is configured in a U-shape so as to support and protect the neck and the back of the head of the infant.

9. The clothing of claim 7, wherein the horizontal core base plate functions as a support so as to prevent a lower portion of the vertical core base plate from hitting the back of the infant and thus hurting the back when the neck of the infant bends back.

10. The clothing of claim 6, wherein the frame structure body further comprises a spring hinge member which is installed between the head base plate and the stopper member to adjust an inclination angle of the head baseplate.

11. The clothing of claim 10, wherein the vertical core base plate further comprises a shoulder fixing base which extends from a lower end of a part to which the bar-shaped hinge member is secured toward both sides.

* * * * *